Figure 1:
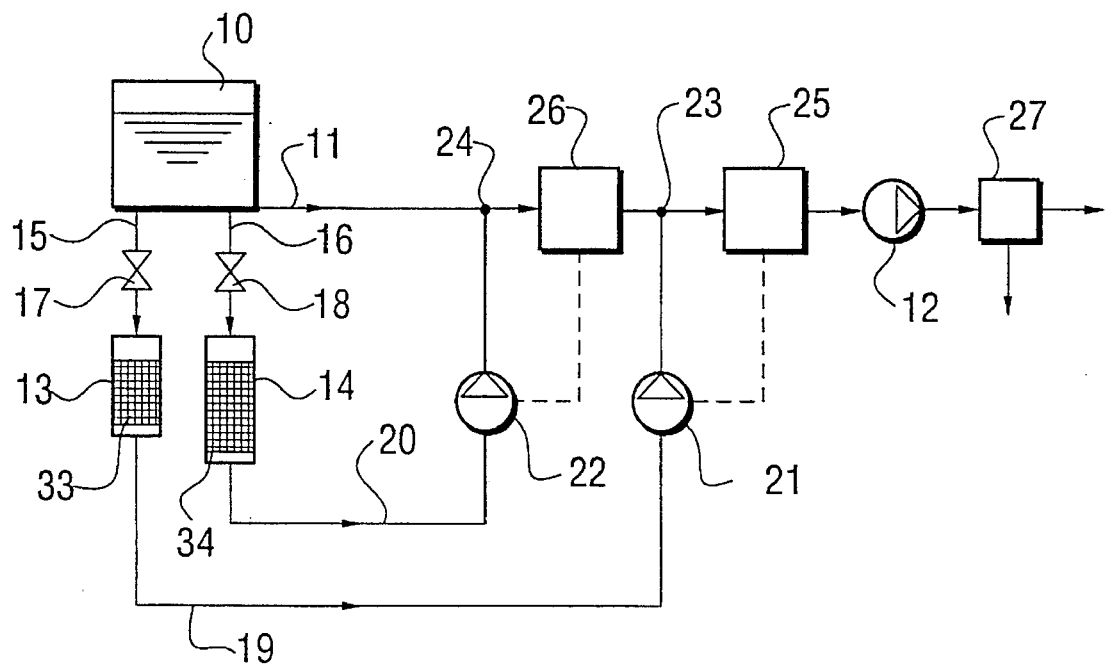

United States Patent [19]
Chevallet et al.

[11] Patent Number: 5,460,446
[45] Date of Patent: Oct. 24, 1995

[54] DEVICE AND METHOD FOR PREPARING SOLUTION FOR MEDICAL USE

[75] Inventors: Jacques Chevallet, Serezin du Rhone; Jacques Burtin, Feyzin; Jacques Gauckler, Lyons, all of France

[73] Assignee: Hospal Industrie, France

[21] Appl. No.: 124,459

[22] Filed: Sep. 22, 1993

Related U.S. Application Data

[63] Continuation of Ser. No. 528,072, May 23, 1990, abandoned.

[30] Foreign Application Priority Data

May 29, 1989 [FR] France .................... 89 07272
May 29, 1989 [FR] France .................... 89 07273
May 29, 1989 [FR] France .................... 89 07274

[51] Int. Cl.⁶ .................................................. B01F 15/02
[52] U.S. Cl. .................... 366/132; 366/136; 366/152.1; 366/163.1; 366/182.4; 137/5; 137/93; 137/268; 137/205; 422/261; 422/282
[58] Field of Search ...................... 366/136, 132, 366/137, 151, 159, 152, 101, 163, 139, 348, 182; 422/255, 261, 282, 283, 292, 234, 264; 222/152; 210/321.71; 137/268, 563, 5, 88, 93, 205, 144, 142; 604/27, 29, 82, 83, 84

[56] References Cited

U.S. PATENT DOCUMENTS

| 1,946,474 | 2/1934 | Banks et al. ........................ 137/88 |
| 2,135,969 | 11/1938 | Donaldson ........................ 422/282 |
| 2,820,701 | 1/1958 | Leslie ........................ 422/283 |
| 3,056,500 | 10/1962 | Carter ........................ 137/563 |
| 3,244,407 | 4/1966 | Obergfell et al. ........................ 366/136 |
| 3,266,870 | 8/1966 | Cianflone, Jr. ........................ 422/282 |
| 3,386,808 | 6/1968 | Handeland ........................ 422/282 |
| 3,474,817 | 10/1969 | Bates et al. ........................ 422/282 |
| 3,539,116 | 11/1970 | Podmore ........................ 366/136 |
| 3,595,395 | 7/1971 | Lorenzen ........................ 422/282 |
| 3,820,014 | 6/1974 | Ludt ........................ 137/5 |
| 4,045,004 | 8/1977 | Berger ........................ 366/136 |
| 4,202,760 | 5/1980 | Storey et al. ........................ 210/321.72 |
| 4,250,910 | 2/1981 | King ........................ 137/268 |
| 4,293,409 | 10/1981 | Reide et al. ........................ 210/321.72 |
| 4,299,501 | 11/1981 | Patil et al. ........................ 366/136 |
| 4,339,232 | 7/1982 | Campbell ........................ 137/205 |
| 4,339,332 | 7/1982 | Jasperson ........................ 422/282 |
| 4,395,130 | 7/1983 | Kutowy ........................ 366/137 |
| 4,482,704 | 11/1984 | Luetzelschwab ........................ 366/136 |
| 4,498,784 | 2/1985 | Bernhardsson et al. ........................ 366/136 |
| 4,580,904 | 4/1986 | Hacheney ........................ 366/137 |
| 4,664,891 | 5/1987 | Cosentino et al. ........................ 366/159 |
| 4,734,198 | 3/1988 | Harm et al. ........................ 210/321.72 |
| 4,784,495 | 11/1988 | Jonsson et al. ........................ 366/160 |
| 4,857,355 | 8/1989 | Gregg ........................ 366/136 |
| 4,908,190 | 3/1990 | Maglio et al. ........................ 422/282 |
| 5,053,206 | 10/1991 | Maglio et al. ........................ 422/282 |

FOREIGN PATENT DOCUMENTS

| 0278100 | 8/1988 | European Pat. Off. . |
| 2517984 | 12/1981 | France . |
| 2569560 | 3/1986 | France . |
| 2114122 | 3/1971 | Germany ........................ 137/88 |

Primary Examiner—David Scherbel
Assistant Examiner—Tony G. Soohoo
Attorney, Agent, or Firm—Finnegan, Henderson, Farabow, Garrett & Dunner

[57] ABSTRACT

A device for preparing a solution for medical use from a liquid and at least one powdered or crystallized salt, comprising:
a main line (11) having a first end connected to a source (10) of liquid and a second end for delivering the solution,
at least one secondary line (15, 19; 16, 20) joined as a by-pass to the main line (11), this secondary line comprising a reservoir (13, 14) containing a powdered or crystallized salt and having an inlet opening and an outlet opening situated respectively at a high point and a low point of the reservoir (13, 14),
means (12, 21, 22) for causing liquid to circulate in the lines,
means (17, 21; 18, 22) for producing the immersion of the powdered or crystallized salt in the reservoir (13, 14).

13 Claims, 2 Drawing Sheets

DEVICE AND METHOD FOR PREPARING SOLUTION FOR MEDICAL USE

This is a continuation of application Ser. No. 07/528,072, filed May 23, 1990, now abandoned.

The present invention concerns a device for preparing solutions for medical use by mixing a liquid with at least one powdered or crystallized salt. These solutions may be used in particular for haemodialysis, haemofiltration or haemodiafiltration. Such a device allows the on-line preparation of the dialysis liquid necessary for haemodialysis or for haemodiafiltration or of substitute liquids for the blood ultrafiltrate taken from the patient, required for haemofiltration or haemodiafiltration.

A device is known from the European Patent Application 278 100 for preparing a solution for medical use from water and at least one powdered salt comprising in particular:

a main line having a first end connected to a source of water and a second end for delivering the solution;

at least one secondary line joined as a by-pass to the main line, this secondary line comprising a reservoir containing a powdered salt and having an inlet opening and an outlet opening preferably situated respectively at a high point and a low point of the reservoir;

means for causing the liquid to circulate in the lines.

The set of the lines is at atmospheric pressure. With this arrangement, it has been noted that the water thus circulating from top to bottom in the reservoir has a tendency to create preferred paths in the powdered salt, and that as the salt is humidified, it forms local agglomerates which are relatively difficult to dissolve. These two phenomena—the creation of preferred paths and the formation of agglomerates—are unwelcome in that they prevent the regular and complete dissolution of the salt necessary for proper progress in preparing an on-line solution.

The object of the present invention is thus a device for preparing a solution for medical use which allows a steady dissolution of the salt irrespective of its coefficient of solubility.

To attain this object, provision is made in accordance with the invention, for a device of the type mentioned above, comprising means for immersing the powdered (or crystallized) salt in the salt reservoir.

Because of this arrangement, the salt remains permanently in the fractional state and the solution which is drawn off from the reservoir has a substantially constant concentration which is that of saturation in the case of the salts generally used for the preparation of solutions for medical use, sodium chloride and sodium bicarbonate in particular.

According to one mode of embodiment of the invention, the means for producing the immersion of the powdered salt comprise means for obturating the secondary line arranged up-line from the reservoir and pumping means disposed down-line from the reservoir.

Because of this arrangement, it is possible, before proceeding with the initial filling of the lines, to remove the air contained in the reservoir, so that at the time of the initial filling, the reservoir is totally filled with water and subsequently remains filled.

According to another mode of embodiment of the invention, the means for producing the immersion of the powdered salt in the water comprise means for pressurising the reservoir.

Because of this arrangement, the depth of water in the reservoir may be adjusted by regulating the air pressure in the reservoir so that, at the time of the initial filling, the water level is established above the upper surface of the powdered salt.

According to one characteristic of the invention, the secondary line comprises a loop comprising the reservoir and means for causing the liquid to circulate in the loop in a closed circuit.

Because of this arrangement, the flow of the liquid in the loop is independent of the flow in the rest of the device and this flow can be adjusted so that, at any time, irrespective of the coefficient of the solubility of the salt, the solution circulating in the loop is a saturated solution.

According to another characteristic of the invention, the junction point of the main line with the section of the secondary line connected to the inlet opening of the reservoir is situated down-line, in relation to the direction of the circulation of the liquid in the main line, from the junction point of the main line with the secondary line connected to the outlet opening of the reservoir.

This arrangement is particularly advantageous in the case of salts having a low coefficient of solubility since, by allowing recirculation in the secondary line, it has the result of raising the concentration of the liquid circulating in the secondary line.

Other characteristics and advantages of the present invention will emerge on reading the following description given in relation to the attached drawings wherein:

FIG. 1 schematically represents a first mode of embodiment of the device in accordance with the invention.

Figure 2:
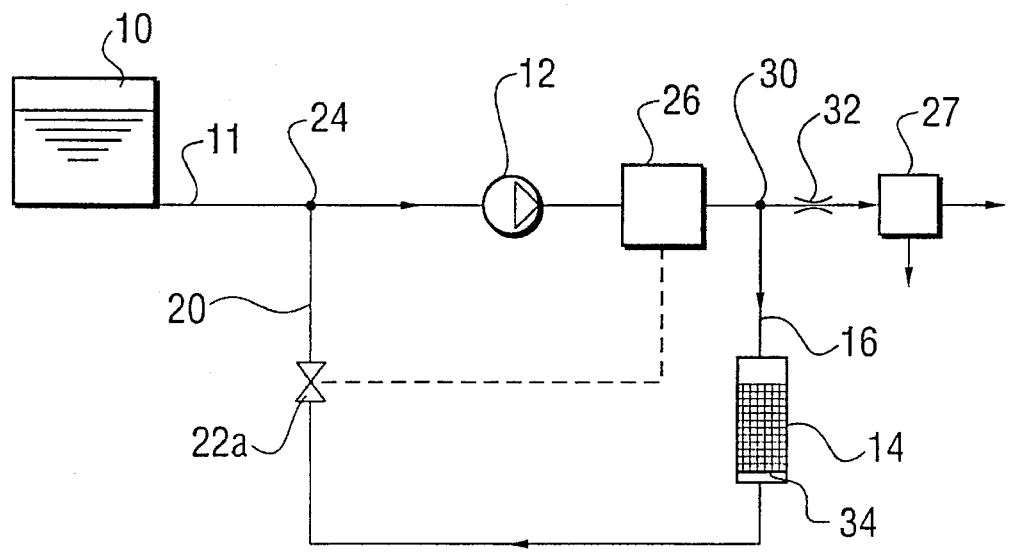
Figure 3:
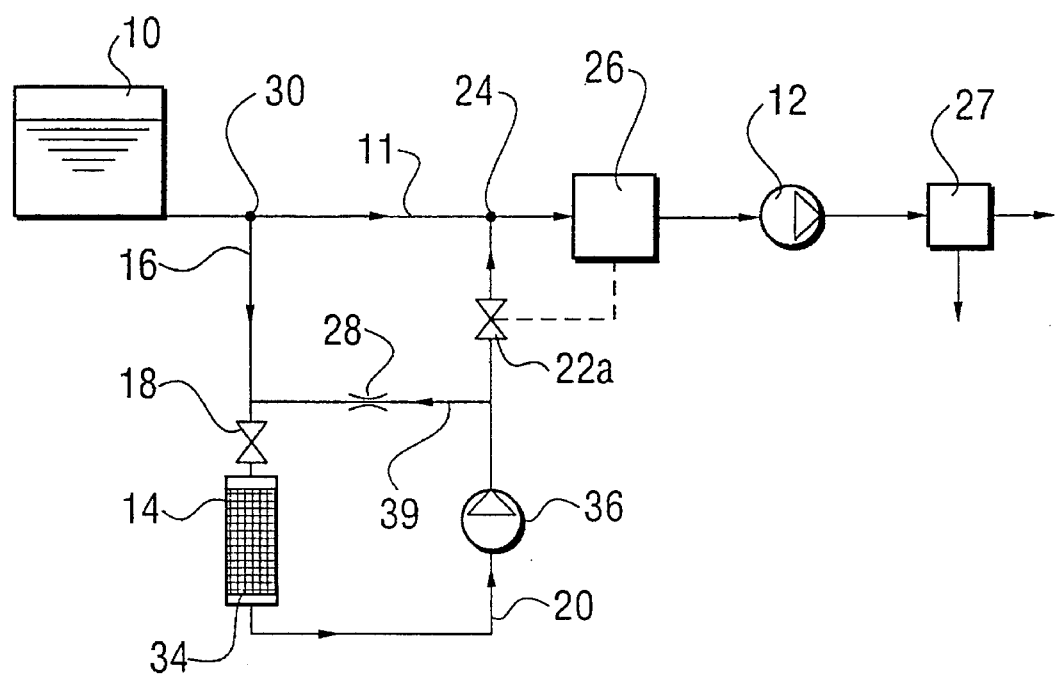
Figure 4:
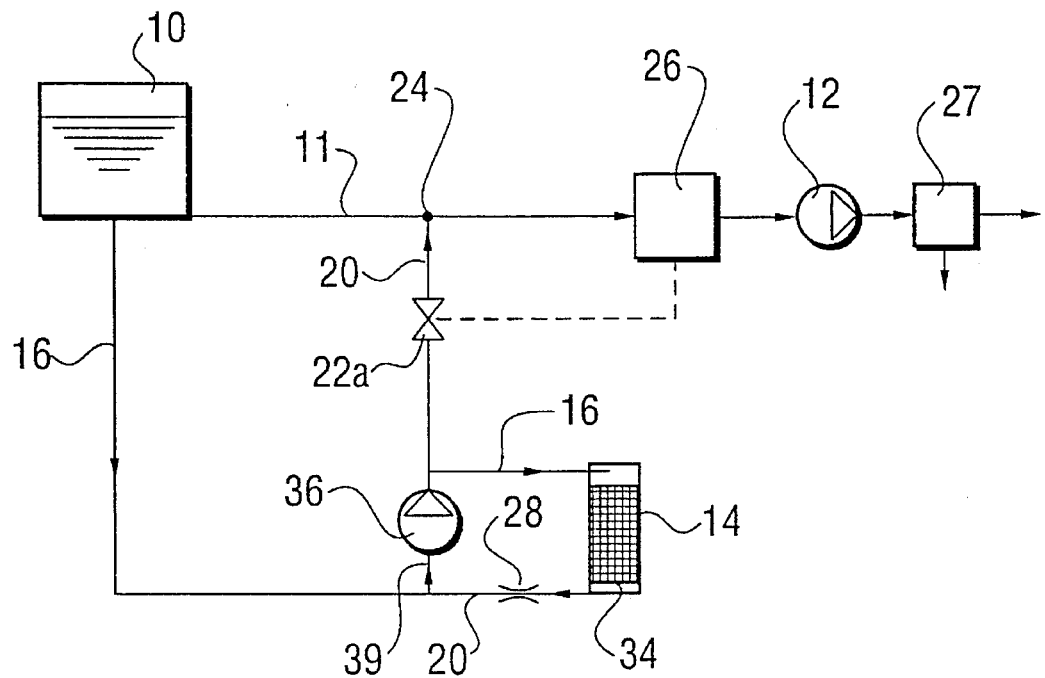

FIG. 2 schematically represents a second mode of embodiment of the device in accordance with the invention;

FIG. 3 schematically represents a third mode of embodiment of the device in accordance with the invention;

FIG. 4 schematically represents a fourth mode of embodiment of the device in accordance with the invention.

Similar elements of the various modes of embodiment of the device in accordance with the invention are designated below by the same reference numerals. Moreover, for greater clarity, only the elements essential for the comprehension of the present invention have been shown in the Figures, by deliberately disregarding all the accessories used in practice, such as devices for heating, degassing, disinfection, cleaning, sterilising, specimen taking etc. which are conventional.

The device represented in FIG. 1 comprises a main line 11 having one end connected to a source 10 of liquid which may be water or a solution and whose other end is connected to a unit 27 for the on-line dispensing and control of the solution for medical use. A pump 12, arranged on the main line, ensures the circulation of the liquid in this line, from the source of the liquid 10 towards the dispensing unit 27. Two secondary lines, of similar structure, are connected in parallel to the main line 11, each of these secondary lines forming a by-pass to the main line.

Each secondary line comprises a reservoir 13 (14) containing a kind of powdered salt (sodium bicarbonate, sodium chloride for example), this reservoir having an inlet opening connected by a tube 15 (16) to the source 10 of the liquid and an outlet opening connected by a tube 19 (20) to the main line 11, at a junction point 23 (24). An obturating device, such as a valve 17 (18) is arranged in the tube 15 (16), that is to say, up-line from the reservoir 13 (14) in relation to the direction of circulation of the liquid in the secondary line, and a pump 21 (22) is arranged on the tube 19 (20), that is to say, down-line from the reservoir 13 (14). As it operates, the pump causes the liquid in the secondary line to circulate towards the junction point 23 (24).

The inlet and outlet openings of the reservoirs 13, 14 are respectively situated at a high point and a low point of these reservoirs. A grille 33 (34) disposed in the bottom portion of each reservoir 13 (14) prevents the undissolved salt from flowing out via the tube 19 (20).

Two elements 25, 26 for measuring the salt concentration of the liquids flowing in the main line 11 are arranged in the duct 11 respectively down-line from the junction points 23, 24. These measuring elements 25, 26 control the pumps 21, 22 according to the instruction values determined by the clinician, whilst the on-line dispensing and control unit 27 shunts the solution produced towards the drain as long as this solution does not have the required concentration of the various salts.

The operation of the device described above is as follows: the initial filling (priming) of the primary and secondary lines with the liquid contained in the reservoir 10 is preceded by a step placing the reservoirs 13, 14 under a partial vacuum. To do this, the secondary lines are obturated up-line from the reservoirs 13, 14 by means of valves 17, 18 and the pumps 21, 22 are operated so as to place the reservoirs 13, 14 at low pressure in relation to the source 10 of liquid (where, for example, a pressure equal to or higher than atmospheric pressure prevails). When the required vacuum level is reached, the valves 17 and 18 are opened and the secondary lines are completely filled with liquid so that the powdered salts contained in the reservoirs 13, 14 are completely immersed and remain so until they are totally dissolved.

FIG. 2 represents a second mode of embodiment of the device in accordance with the invention comprising a main line 11 and a secondary line forming a by-pass to the main line. As before, the main line 11 has its ends respectively connected to a source 10 of liquid (water or solution) and to a unit 27 for the on-line dispensing and control of the solution for medical use.

The secondary line comprises a reservoir 14 for powdered salt having an inlet opening connected via a tube 16 to the main line 11 at a junction point 30, and an outlet opening connected via a tube 20 to the main line 11, at a junction point 24. The junction point 30 is situated down-line from the junction point 24 with respect to the circulation direction of the liquid in the line 11. The inlet and outlet openings of the reservoir 14 are respectively situated at a high point and a low point of the reservoir.

The circulation of the liquids in the main and secondary lines is produced by a pump 12 arranged in the line 11 between the junction points 24 and 30. The circulation direction of the liquid in the secondary line, along which the liquid partly recirculates in the lines, is imposed by a loss of pressure occurring in the main line 11 down-line from the junction point 30. This pressure loss may be produced by a device not specifically provided for this purpose, the dispensing and control unit 27, for example. It may also be produced by specific means, such as the constriction device 32. It is this loss of pressure which also allows the pressurisation of the reservoir 14 under the action of the pump 12, and hence the filling of the reservoir 14 to the desired level.

Like the earlier device, this device comprises an element 26 for measuring the salt concentration of the solution circulating in the main line. This element is disposed down-line from the junction point 24 and it controls a valve 22a arranged in the secondary line down-line from the reservoir 14 in such a way that the solution circulating in the main line should have the desired salt concentration.

The operation of this device for preparing a solution for medical use is as follows: the initial filling of the main and secondary lines is produced by the operation of the pump 12 which causes the liquid coming from the source 10 to circulate, and pressurises a part of the lines, including the reservoir 14. A proper adjustment of the pressure loss down-line from the junction point 30 by means of the constriction device 32 allows sufficient pressurisation of the reservoir to guarantee the immersion of the salt contained in the reservoir 14 when the device is started. The on-line dispensing and control unit 27 shunts the solution produced towards the drain as long as this solution does not have the required salt concentration.

FIGS. 3 and 4 represent two variants of the device in accordance with the invention, their main common point being that their secondary line comprises a loop comprising the reservoir for powdered salt and means for causing the liquid to circulate in the loop in a closed circuit.

In the device represented in FIG. 3, the loop is closed by a tube 39 connecting the tube 16 to the tube 20 (which, as before, respectively connect the inlet and outlet openings of the reservoir 14 to the main line 11). In the loop thus formed, there are disposed a valve 18 in the tube 16, that is to say, up-line from the reservoir 14, a pump 36 on the tube 20, that is to say, down-line from the reservoir 14, and a constricting device 28 on the tube 39. The measuring element 26 disposed on the main line 11 down-line from the junction point 24 of the tube 20 to the main line controls a valve 22a disposed in the tube 20 down-line from the loop.

The device described above operates as follows: before the main and secondary lines are filled, the valve 18 is closed, the valve 22a is opened and the pump 36 is started so as to create a partial vacuum in the reservoir 14. When the desired vacuum level has been obtained, the valve 18 is opened. When the lines are completely filled, the valve 22a is closed and the liquid then circulates in a closed circuit in the loop under the effect of the pump 36 whose delivery is adjusted to ensure that the liquid in the loop is rapidly saturated. The valve 22a is then opened and a portion of the saturated solution contained in the loop flows into the main line 11 where it is mixed with the liquid drawn off from the source 10 by the pump 12, while it is simultaneously replaced in the loop by liquid drawn off by the pump 36 from the source 10 via the tube 16. The function of the constricting element 28 disposed on the tube 39 is to promote the intake of liquid and the emergence of the solution into/out of the loop when the valve 22a is opened. As in the devices described above, the on-line dispensing and control unit 27 shunts the prepared solution towards the drain as long as the salt concentration has not reached the required level.

The device represented in FIG. 4 is different from the one described above in that the secondary line is closed to form a loop by a tube 39 which is a tube section common to the tubes 16 and 20, in which section there is disposed a pump 36 that draws the liquid coming from the source 10 and the solution emerging from the reservoir 14 and delivers it towards the main line 11 and the inlet of the reservoir 14. The loop moreover comprises a constricting element 28 disposed down-line from the reservoir 14 in the tube 20. The measuring element 26 disposed in the main line 11 down-line from the junction point 24 of the tube 20 with the main line controls a valve 22a disposed in the tube 20 down-line from the loop.

The operation of the device described above is as follows: for the initial filling of the lines, the valve 22a is closed and the pumps 36 and 12 are started. The pump 36 fills the secondary line with the liquid from the source 10 whilst pressurising the reservoir 14, thanks to the pressure loss produced by the constricting element 28. As a result of this pressurisation which can be adjusted by any known means, the salt contained in the reservoir is immersed when the filling of the secondary line has been completed. As soon as this filling has been completed, the pump 36 produces the circulation of the liquid in the loop in a closed circuit at a rate of flow chosen so that it should be quickly saturated.

The operation of this device under steady conditions does not differ from that of the device described with reference to FIG. 3.

The present invention is not limited to the examples described above and it can accommodate variants. In particular, in the circuits for preparing the solution comprising several secondary lines, these secondary lines can be joined in series to the main line and not only in parallel as in the mode of embodiment represented in FIG. 1.

We claim:

1. A method for preparing in-line a medical solution in a medical device having a main line with a first end connected to a source of liquid and a second end for delivering the medical solution, the device also including at least one secondary line having a first portion connecting the source of liquid to an inlet of a reservoir containing a soluble particulate product and a gas, and having a second portion connecting an outlet of the reservoir to the main line at a connecting point between the liquid source and the second end, the method comprising the steps of:

occluding the first portion of the secondary line to prevent liquid flow into an initially liquid-free reservoir containing particulate product;

generating a predetermined partial vacuum by pumping gas from the reservoir using a pump located in the secondary line downstream of the reservoir;

opening the first portion of the secondary line to permit liquid to flow from the source into the reservoir after the step of generating a partial vacuum;

filling the reservoir to at least a first level immersing the particulate product in the flowing liquid in response to the predetermined partial vacuum;

flowing the liquid through the second portion of the secondary line to provide a first solution of the particulate product at the connecting point; and flowing the liquid from the source through the main line toward the connecting point; and mixing the flowing liquid with the first solution to form a second solution at the second end of the main line.

2. The method of claim 1, further comprising the step of recirculating the first solution through the reservoir before mixing the first solution with the flowing liquid and after the steps of occluding, generating, opening, and filling, so that the first solution is a saturated solution of the particulate product.

3. The method of claim 1, further comprising the steps of:

sensing a concentration of the particulate product in the second solution;

comparing the sensed concentration to a desired concentration; and adjusting a flow rate of the liquid in the secondary line to substantially equalize the sensed concentration with the desired concentration.

4. The method of claim 3, further comprising the step of discarding the second solution at times when the sensed concentration is not substantially equal to the desired concentration.

5. A method for preventing preferential liquid paths and agglomerates in a particulate product disposed in a reservoir containing a gas, the method comprising the steps of:

providing a reservoir containing particulate product;

fluidly connecting the reservoir in a line to a source of liquid, the line having a valve;

closing the valve to cut off liquid between the source and the reservoir;

withdrawing gas from the reservoir using a pump located in the line downstream of the reservoir to cause in the reservoir at least a partial vacuum sufficient to cause at least the immersion of the particulate product in the reservoir upon subsequent opening of the valve;

opening the valve so that the liquid rushes into the reservoir from the source, to substantially cover the particulate product and to thereby prevent preferential paths and the formation of agglomerates of particulate product; and dispensing a solution of the particulate product from the reservoir, whereby the liquid flows in a substantially unobstructed manner from the source to the reservoir, mixes with the particulate product, and exits the reservoir through an outlet therein.

6. A device for preparing a medical solution using a source of liquid and a particulate product susceptible to formation of agglomerates and preferential paths of liquid therethrough, the device comprising:

a main line having an inlet end for fluid connection to the source of the liquid and a discharge end for delivering a medical solution;

at least one secondary line bypassing a section of the main line for conveying the liquid, said at least one secondary line having a first upstream end and second end downstream from the first end, the first end being fluidly connected to one of said main line and said source at a first position proximate to said inlet end, and the second end being fluidly connected to said main line at a second position downstream of the first position so that a section of the main line is bypassed by said at least one secondary line;

a reservoir having an interior volume and disposed in said at least one secondary line downstream of the source, a portion of the secondary line being disposed between the first position and the reservoir, the reservoir for holding and dispensing the particulate product into said liquid in said secondary line;

means for preventing preferential paths of said liquid through the particulate product in said reservoir and for preventing agglomerates of the particulate product, said preventing means including a valve disposed in said portion of the secondary line upstream of the reservoir and downstream of the source, the valve being selectively adjustable between an open position permitting fluid flow from the source to the reservoir through said portion of the secondary line and a closed position cutting off fluid flow from the source to the reservoir by blocking said portion of the secondary line, the preferential path preventing means also including a pump disposed in the secondary line downstream of the reservoir on a side of the reservoir opposite the valve between the reservoir and the second position, the pump having a suction side communicating with the reservoir to evacuate the reservoir when the valve is in the closed position, to thereby permit the reservoir to fill with liquid from the source when the valve is subsequently moved to the open position;

means for detecting the concentration of product in said main line; and control means for preventing solution from exiting through said discharge end of said main line when the concentration of product therein is not at a preselected level.

7. A device according to claim 6, wherein said pump and said obturation device cooperate to cause a partial vacuum in said reservoir.

8. A device according to claim 6, wherein said concentration detecting means includes a concentration detector disposed in said main line downstream of said connection point.

9. A device according to claim 6, wherein said at least one secondary line includes two secondary lines, one of said secondary lines being connected to the main line at a first connection point, and the other of said secondary lines being connected to said main line at a second connection point.

10. A device according to claim 9, wherein said concentration detecting means includes a first concentration detector disposed in said bypassed section of said main line, and a second concentration detector disposed in a non-bypassed section of said main line.

11. A device according to claim 9, further including a second pump, said second pump being located in the other of the two secondary lines.

12. A medical solution preparation device, comprising:

a main line having an inlet end and an outlet end, said inlet end being fluidly connectable to a source of fluid;

at least one secondary line connected to said main line, bypassing a section of said main line for conveying the liquid, said at least one secondary line having a first upstream end and second end downstream from the first end, the first end being fluidly connected to one of said main line and said source at a first position proximate to said inlet end, and the second end being fluidly connected to said main line at a second position downstream of the first position so that a section of the main line is bypassed by said at least one secondary line;

a reservoir having an interior space and disposed in the secondary line downstream of the source, a portion of the secondary line being disposed between the first position and the reservoir, the reservoir for holding a substance to be dispensed; and means for reducing an amount of air in said interior space in said reservoir, said reducing means including a valve for selectively cutting off fluid flow from the source to the reservoir by blocking said portion of the secondary line located between the reservoir and the source of fluid, the valve being disposed in said portion of the secondary line upstream of the reservoir and downstream of the source, the valve being selectively adjustable between an open position permitting fluid flow through said portion of the secondary line and a closed position cutting off fluid flow through said portion of the secondary line, the reducing means also including a pump, the pump being disposed in the secondary line downstream of the reservoir on a side of the reservoir opposite the valve between the reservoir and the second position, the pump having a suction side communicating with said reservoir to evacuate the reservoir when the valve is in the closed position, to thereby permit the reservoir to fill with liquid from the source when the valve is subsequently moved to the open position.

13. A device according to claim 12, wherein the pump reduces the amount of air occupied interior space by producing a partial vacuum in the reservoir.

* * * * *